Feb. 7, 1950 W. T. KIRKMAN, JR Plant Pat. 920
PEACH TREE
Filed Dec. 8, 1947
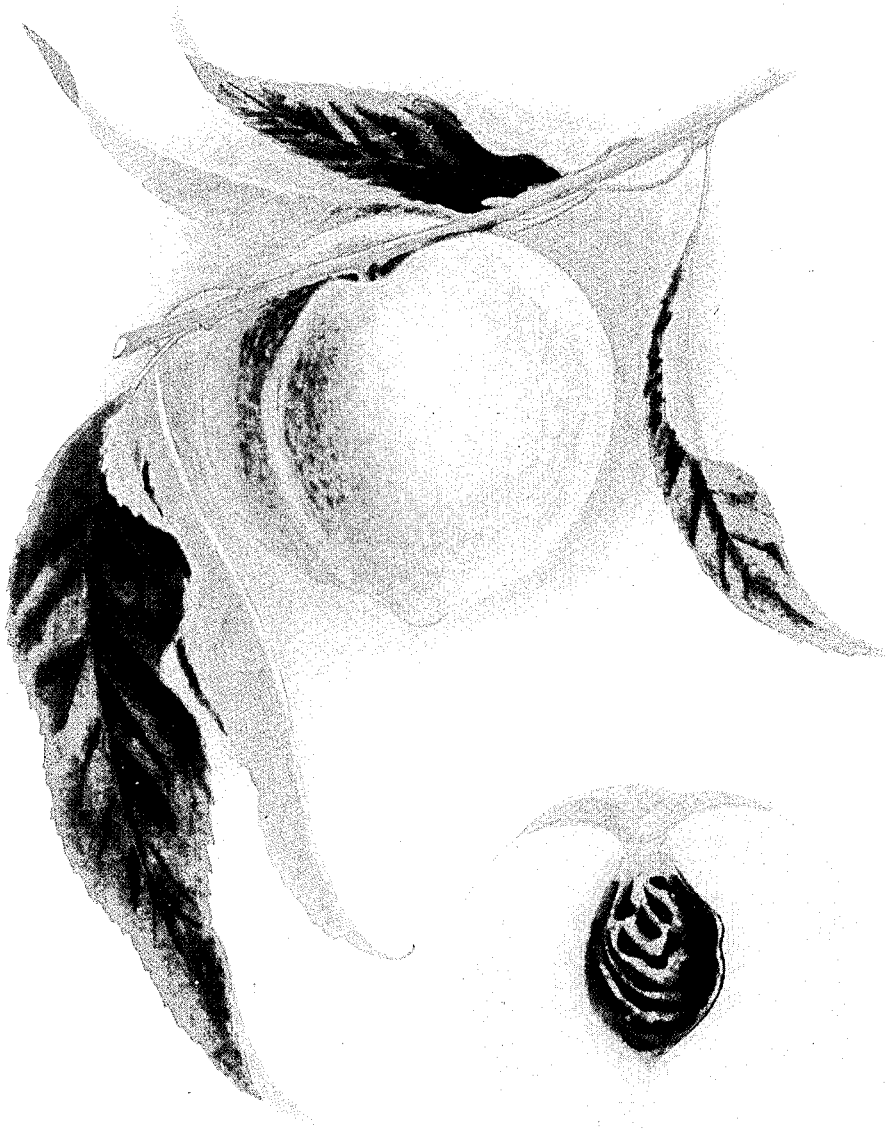
WITNESS
Addison J. Avery
INVENTOR
Wm. T. Kirkman Jr.
Webster & Webster
ATTYS.

Patented Feb. 7, 1950

Plant Pat. 920

UNITED STATES PATENT OFFICE

920

PEACH TREE

William T. Kirkman, Jr., Tracy, Calif., assignor to Kirkman Corporation, Tracy, Calif., a corporation of California Application December 8, 1947, Serial No. 790,333

1 Claim. (Cl. 47—62)

This discovery relates to a new and distinct variety of peach tree which bears fruit having marked commercial advantages, both as to ripening and shipping characteristics.

The tree bears fruit which is a large, late ripening freestone, and such tree and its fruit are described herein as compared to the Kirkman Gem, as embraced by U. S. Plant Patent No. 506, dated March 17, 1942.

The present discovery is a variety which resulted from an open pollinated seedling of the Kirkman Gem peach tree, and the discovery was made in the applicant's experimental orchard near Borden Station, Madera County, California.

Bud wood from the aforesaid seedling was top worked on orchard trees (John Rivers Nectarines) in the aforesaid experimental orchard, and these top workings are now in bearing; such asexual reproductions of the variety evidencing all of the desirable characteristics of the parent.

The present variety, while similar in some respects to the Kirkman Gem, is distinct:

(*a*) In that the fruit may hang on the tree for a considerable length of time after ripening without becoming over-ripe, which makes possible picking over a longer period, or the awaiting of all the fruit to ripen, and harvesting at one time.

(*b*) In that the date of last picking of the fruit (which may be the date of only picking of the variety, as per (*a*) above), is somewhat later than the Kirkman Gem.

(*c*) In that the deep reddish suture line of the Kirkman Gem is absent, which suture line ripened earlier than the remainder of the flesh of the fruit, thus limiting to some extent the period which the fruit could be kept unspoiled after picking.

(*d*) In that the tree of the present variety is more vigorous than the Kirkman Gem.

Fig. 1 of the drawing is a perspective view, in natural color, of one of the peaches of the new variety in association with a twig including leaves.

Fig. 2 is a sectional elevation of the peach taken on the suture line.

The following description sets forth in detail the characteristics of the new and distinct peach tree and its fruit.

Color identification in this specification is, to a certain extent, made by direct comparision with Maerz and Paul Dictionary of Color, and indicia corresponding to plate, letter, and number, respectively, of said dictionary are set forth following color descriptions.

*Tree.*—The tree is of medium size, vigorous, spreading, open, and round-topped; the vigor of the tree being somewhat greater than that of the Kirkman Gem. The tree has medium productivity, but is a regular bearer.

The trunk is of medium size and medium texture; the branches being likewise of medium size, smooth, and brown (6–H–11) in color. The lenticels are few in number and small in size.

*Leaves.*—The leaves average 6¾″ in length and 1¼″ in width; such leaves being of medium size, acuminate, lanceolate, and acutely pointed. Additionally, the leaves are of medium thickness, and smooth, being dark green (22–L–7) on the top side, and relatively light green (22–K–4) on the under side.

The margin of the leaves is glandular and crenate, and the petiole is short and thick; the glands, averaging four in number, being opposite, of medium size, reniform, green, and positioned on the petiole near the leaf blade.

*Flower buds and flowers.*—The flower buds are of medium size and length, obtuse, plump, appressed to free, and pubescent. The flowers are of large size and pink, being substantially the same as on the Kirkman Gem.

*Fruit.*—The fruit is of large size, averaging axially 3″ to 3⅛″, and averaging 3¼″ transversely in the suture plane. In form the fruit is uniform, symmetrical and globose.

The suture is a cacao brown (5–B–11) inconspicuous line, with a slight depression beyond the pistil point, and is distinct from the suture of the Kirkman Gem in that the deep reddish suture line of the latter is absent. This is an advantage, for the reason that the deep reddish suture of the Kirkman Gem has a tendency to ripen ahead of the remainder of the flesh of the fruit, which naturally limits the keeping time after picking. This characteristic is wholly absent from the present variety, wherein the yellow suture line ripens evenly with the remainder of the fruit, which is desirable.

The ventral surface is rounded and the lips are equal. The cavity is flaring and rounded, being circular to elongated in the suture plane, and averaging ½″ deep and 1½″ in breadth. The markings are smooth. The base is truncate; the apex short, mammiform, and rounded; and the pistil point is apical.

The skin is of medium thickness, tender, and relatively tenacious to the flesh, with no tendency to crack. In color the skin is deep yellow (11–L–9); the reddish brown mottling adjacent the suture being relatively dark (5–L–11), while the reddish brown mottling remote from the suture is relatively light (7–L–1). Down is moderate and short.

The flesh of the fruit is yellow (9–L–7), streaked with red (3–L–10) next to the stone. The surface of the pit cavity is red with yellow fibers, amygdalin is scant, and the juice is moderate. The texture of the flesh is quite firm, fine, and meaty. Fibers are few, fine, and tender. The flesh ripens evenly, and the flavor is sub-acid to mild, with aroma wanting.

The stone in free and parts from the flesh smoothly; such stone being of medium size, averaging 1½″ to 1⅝″ in length, 1⅛″ to 1¼″ in breadth, and ¾″ in thickness. The form of the stone is oval; the base is straight to oblique; the hilum is oval; and the apex acute to acuminate. The sides are equal, and the surface is irregularly furrowed throughout; being ridged toward the apex and pitted toward the base. The ridges are rounded. The pits are elongated, and the dorsal edge is narrow with shallow, narrow grooves throughout. The ridges are interrupted. The color of the stone is a deep brown (48–L–1), and such stone has slight tendency to split.

*Ripening period.*—The fruit of this variety ripens mid-September to mid-October; the date of last picking thus being somewhat later than the Kirkman Gem, whose date of last picking is before the end of September. In addition, to the date of last picking being later than that of the Kirkman Gem, the present variety is further characterized by the fact that the fruit may be left on the tree for a considerable length of time after ripening, and yet without becoming over-ripe. This makes it possible for the picking to be deferred, if desired, until all of the fruit is ripe, which may be toward the date of last picking. The fruit is thus available for the late market.

Such fruit is further characterized by the fact that it keeps well after being picked, being capable of withstanding shipment to distant points. This advantage is enhanced by the absence of the early ripening suture line of the Kirkman Gem, as previously explained.

The variety has medium resistance to insects, and good resistance to plant diseases.

*Use.*—The fruit thus is an excellent market variety, well adapted for commercial shipping, as an eating fruit, and as a canning fruit.

The characteristics of this new variety of peach tree and its fruit as described are typical as grown near Madera, California, but may be subject to variations if grown in different localities, with varying conditions of soil or climate.

Having thus described the instant new variety of peach tree and its fruit, what I claim as new and useful and desire to secure by Letters Patent is:

The new and distinct variety of peach tree, as described and illustrated, characterized, in comparison with the Kirkman Gem, by the later ripening period of the fruit; the ability of its ripened fruit to remain on the tree a considerable length of time without spoiling; the yellow suture line which ripens evenly with the fruit as distinguished from the deep reddish early ripening suture line of the Kirkman Gem; and the greater vigor of the tree.

WILLIAM T. KIRKMAN, JR.

No references cited.